United States Patent
Turner

(10) Patent No.: US 12,133,943 B2
(45) Date of Patent: Nov. 5, 2024

(54) CONTROL SYSTEM

(71) Applicant: Spectrum Medical Ltd, Gloucester (GB)

(72) Inventor: Stephen Turner, Gloucester (GB)

(73) Assignee: Spectrum Medical Ltd., Gloucester (GB)

( * ) Notice: Subject to any disclaimer, the term of this patent is extended or adjusted under 35 U.S.C. 154(b) by 458 days.

(21) Appl. No.: 16/856,386

(22) Filed: Apr. 23, 2020

(65) Prior Publication Data

US 2020/0345914 A1 Nov. 5, 2020

(30) Foreign Application Priority Data

May 3, 2019 (GB) ..................................... 1906300

(51) Int. Cl.
*A61M 1/14* (2006.01)
*A61M 1/16* (2006.01)

(52) U.S. Cl.
CPC ............ *A61M 1/14* (2013.01); *A61M 1/1698* (2013.01); *A61M 2202/0208* (2013.01); *A61M 2202/0225* (2013.01); *A61M 2202/0266* (2013.01); *A61M 2205/3334* (2013.01)

(58) Field of Classification Search
CPC ...... A61M 1/14; A61M 1/1698; A61M 16/10; A61M 16/1005; A61M 16/101; A61M 16/1015; A61M 2016/102; A61M 2016/1025; A61M 16/12; A61M 16/122; A61M 16/125; A61M 16/127
See application file for complete search history.

(56) References Cited

U.S. PATENT DOCUMENTS

| | | | |
|---|---|---|---|
| 3,927,981 A | 12/1975 | Viannay et al. | |
| 4,493,692 A | 1/1985 | Reed | |
| 4,749,551 A | 6/1988 | Borgione | |
| 4,874,581 A | 10/1989 | Sunderland et al. | |
| 5,069,661 A | 12/1991 | Trudell | |
| 5,158,534 A * | 10/1992 | Berry .................. | A61M 1/1698 604/6.14 |
| 5,810,759 A | 9/1998 | Merz | |

(Continued)

FOREIGN PATENT DOCUMENTS

| | | |
|---|---|---|
| CN | 102575811 | 7/2012 |
| EP | 1557185 A1 | 7/2005 |

(Continued)

OTHER PUBLICATIONS

UK Patent Office, Examination Report dated Oct. 26, 2022 for GB Application No. 1906300.7 (2 pages).

(Continued)

*Primary Examiner* — Adam Marcetich
*Assistant Examiner* — Rachel O'Connell
(74) *Attorney, Agent, or Firm* — Sunstein LLP

(57) ABSTRACT

A gas supply control system for an oxygenator of an extracorporeal ventilation system is configured for connection to external gas supply ports for oxygen and nitrogen in the form of air and to create a supply gas output from oxygen and nitrogen. The gas supply control system includes two or more gas output lines and configured to supply the two or more gas output lines with the supply gas output. The flow rates through the gas output lines may be modulated differently.

20 Claims, 4 Drawing Sheets

(56) References Cited

U.S. PATENT DOCUMENTS

| | | | |
|---|---|---|---|
| 6,004,511 | A | 12/1999 | Biscegli |
| 7,278,981 | B2 * | 10/2007 | Ellingboe ............ A61M 1/3623 604/4.01 |
| 8,585,968 | B2 | 11/2013 | Morley et al. |
| 10,512,716 | B2 | 12/2019 | Turner |
| 2006/0144225 | A1 * | 7/2006 | Downie .................... F17C 1/00 95/90 |
| 2007/0077200 | A1 | 4/2007 | Baker |
| 2009/0182258 | A1 * | 7/2009 | Nogueira Sanches ....................... A61M 1/1698 604/4.01 |
| 2010/0101657 | A1 | 4/2010 | Morley et al. |
| 2010/0198014 | A1 * | 8/2010 | Poll ........................ A61B 1/127 600/123 |
| 2010/0224192 | A1 | 9/2010 | Dixon et al. |
| 2014/0216252 | A1 | 8/2014 | Joost et al. |
| 2014/0227134 | A1 | 8/2014 | Joost |
| 2016/0015881 | A1 | 1/2016 | Utsugida et al. |
| 2017/0165293 | A1 * | 6/2017 | Dasse ................. A61M 1/3666 |
| 2017/0368247 | A1 * | 12/2017 | Turner ................. A61M 1/1698 |
| 2018/0344918 | A1 | 12/2018 | Turner et al. |
| 2019/0160217 | A1 | 5/2019 | Marseille et al. |
| 2020/0188571 | A1 | 6/2020 | Gipson |

FOREIGN PATENT DOCUMENTS

| | | | |
|---|---|---|---|
| EP | 1810704 | B1 | 4/2015 |
| GB | 2437254 | | 10/2007 |
| GB | 2485558 | | 5/2012 |
| GB | 2582239 | A | 9/2020 |
| JP | 2001079083 | | 3/2001 |
| JP | 2004160217 | A | 6/2004 |
| JP | 2010213851 | A | 9/2010 |
| JP | 2018500972 | A | 1/2018 |
| WO | 91/16967 | A1 | 11/1991 |
| WO | 2003/092776 | | 11/2003 |
| WO | 2005/118025 | A1 | 12/2005 |
| WO | 2008/107723 | A2 | 9/2008 |
| WO | 2009/141149 | A1 | 11/2009 |
| WO | 2015/008327 | A1 | 1/2015 |
| WO | 2015/047927 | | 4/2015 |
| WO | 2016071691 | | 5/2016 |
| WO | 2016/0878859 | | 6/2016 |
| WO | 2016181189 | | 11/2016 |
| WO | 2017211460 | A1 | 12/2017 |
| WO | 2018026672 | A1 | 2/2018 |
| WO | 2019/035869 | A1 | 2/2019 |
| WO | 2019035869 | | 2/2019 |
| WO | 2019/166823 | | 9/2019 |

OTHER PUBLICATIONS

UK Patent Office, Examination Report dated Jan. 23, 2023 for GB Application No. 1906300.7 (2 pages).
UK Intellectual Property Office, Search Report issued in GB patent application No. GB1906300.7, dated Oct. 31, 2019, 4 pages.
European Patent Office; International Search Report for PCT Application No. PCT/GB2019/050579 dated May 24, 2019 (4 pages).
European Patent Office; International Search Report for PCT Application No. PCT/GB2015/053694 dated May 13, 2016 (6 pages).
Chinese Office Action for CN Application No. 201580075441.0 dated Jun. 4, 2019 (7 pages).
GB Intellectual Property Office; Search Report for GB Application No. 1421498.5 dated May 18, 2015 (1 page).
European Patent Office, European Search Report dated Aug. 26, 2020 for EP Application No. 20168781.1 dated (7 pages).

* cited by examiner

CONTROL SYSTEM

CROSS-REFERENCE TO RELATED APPLICATIONS

This application claims the benefit of UK patent application No. 1906300.7, filed May 3, 2019, the disclosure of which is incorporated herein by reference in its entirety.

FIELD OF THE INVENTION

The present invention relates to an oxygenation gas supply system and corresponding method, for controlling the supply of oxygenation gas to an oxygenator of an extracorporeal blood oxygenation system. More specifically, the present invention relates to an oxygenation gas supply system and method permitting supply of multiple individual oxygenation lines with oxygenation gas, and corresponding methods of operation. The present invention also relates to systems and methods of operating an exhaust system with a sampling line.

BACKGROUND

Extracorporeal perfusion is a process in which blood from a patient is circulated outside the patient's body, to be re-oxygenated and to have its carbon-dioxide levels adjusted, in order to be brought into a condition to be returned to the patient, or to be used for exclusively extracorporeal testing purposes in which the blood is not returned to a patient. More specifically, venous (oxygen-reduced) blood is supplied via an incoming line, or venous line, to an oxygenator in which the blood is oxygenated by exposure to an oxygenation gas in an oxygenator for supply via an outgoing line, or arterial line, back to the patient as arterial blood.

Extracorporeal perfusion is typically used to substitute heart and lung functionality during a medical procedure, e.g. open heart surgery or lung treatment. Extracorporeal blood is brought into a condition for subsequent return to the patient. Blood conditioning includes setting an appropriate temperature, flow rate, line pressure, and mixing with agents such as anti-coagulants. With regard to the oxygen content and carbon dioxide content, this is adjusted in the oxygenator, where blood is exposed to an oxygenation gas via a gas-blood interface through which oxygen is permitted to diffuse into and to be taken up by the blood. The gas-blood interface may be provided by gas-permeable walls of hollow fibres, where gas passes through the inner passage of the hollow fibres, and blood around the outside of the hollow fibres. After blood has left the oxygenator, there is usually no further possibility to increase the blood oxygen content before the blood is administered to a patient. To provide an illustration of the flow rates involved, in adult patients, blood may be circulated at a typical flow rate in the region of 5 litres per minute (lpm). For this and other reasons, many parameters must be controlled to ensure that the blood leaving the oxygenator is appropriately oxygenated and carbon dioxide levels are appropriate.

International patent application PCT/GB2015/053694 by the present applicant, published as WO2016/087859, the contents of which are incorporated by reference, discloses an oxygenation system for a ventilation system comprising a flow control arrangement for controlling the flow rate of the exhaust gas relative to the oxygenation gas. WO2016/087859 also discloses a blender for preparing an oxygenation gas with a high-accuracy oxygen content at low flow rates. The blender and flow control arrangement disclosed in WO2016/087859 can be used to maintain low flow rates of an oxygenation gas while also permitting a high degree of blending accuracy and while permitting the exhaust gas to be withdrawn at an appropriate flow rate that is low, yet higher than the oxygenation gas supply.

As stated in WO2016/087859, even though vacuum may be employed to assist with a controlled exhaust gas removal at low flow rates, the gas flow within the oxygenator is achieved at atmospheric pressure. This is because, at its exhaust side, the oxygenator housing comprises openings to avoid pressurisation and prevent a positive pressure gradient from exhaust side (outlet) to oxygenation gas inlet. A significant outlet-to-inlet pressure gradient could lead to the introduction of gross volumes of gas across the gas-blood interface (typically constituted by gas-permeable gas-exchange fibres), which in turn could lead to gas bubbles forming in the blood, which render the blood unsafe for return to a patient.

The above described hollow fibre oxygenator may comprise several thousand hollow fibres, which would however be understood as being supplied by a common oxygenation gas supply, such that each fibre is supplied with supply gas of effectively the same composition and flow rate. International Patent Application No PCT/GB2019/050579 by the present applicant discloses a 'multi-region' oxygenator design in which the gas-blood interface is separated into two or more individually supplyable gas-blood interface regions, or 'chambers', providing the oxygenator with a capability of exposing blood passing through the oxygenator in a given oxygenation cycle to different oxygenation gas conditions during the given oxygenation cycle.

The present invention is concerned with providing additional options for blood oxygenation during extracorporeal perfusion.

SUMMARY OF THE INVENTION

In accordance with a first aspect of the invention, there is provided a gas supply system for an oxygenator as defined by claim 1.

The gas supply system is for an oxygenator of an extracorporeal ventilation system. The gas supply control system is configured for connection to external gas supply ports to receive supplied oxygen and supplied nitrogen, wherein the gas supply control system comprises a configuration allowing it to create a supply gas output from a predetermined portion of supplied oxygen and from a predetermined portion of supplied nitrogen. The gas supply control system comprises two or more gas output lines. The gas supply control system comprises a configuration allowing it to provide the supply gas output through one of the gas output lines and a configuration allowing it to provide the supply gas output through a plurality of the gas output lines.

In some embodiments, the gas supply system comprises a configuration allowing it to modulate flow rates through the gas output lines differently.

It is understood that the oxygenator is for an extracorporeal ventilation system and comprises a gas passage and a blood passage arranged to allow gas exchange of an oxygenation gas supply with blood via a gas-blood interface, wherein the gas passage leads from a gas inlet zone via the gas-blood interface to a gas exhaust zone, and wherein the blood passage leads from a blood inlet via the gas-blood interface to a blood outlet. The gas supply control system is intended to supply gas, so-called sweep gas, the gas inlet zone of the oxygenator. As such, the gas supply control system is understood to be located upstream of the oxygenator.

Throughout literature relating to extracorporeal oxygenators, reference is typically made to a 'sweep' gas, or supply gas, that is provided to the oxygenator. The present specification focuses on equipment connected between a hospital gas source and the oxygenator gas inlet. To avoid a confusion in terminology, the present specification refers to a gas "source" if this is a hospital gas supply (port, canister, or similar) provided to the present system. Herein, an "intake line" is an element receiving, or configurable to receive, a gas supplied by a hospital source. An "output line" is an element providing, or configurable to provide, a gas towards the oxygenator inlet. The expressions "exhaust" and "outlet" designate the gas exit route of an oxygenator.

The gas supply system is thought to be particularly useful for an oxygenator comprising separately supplyable interface regions of the gas-blood interface. Such an oxygenator type has been developed by the present applicant and is described in International Patent Application No PCT/GB2019/050579.

To provide an illustrative example, the gas-blood interface of an oxygenator may be provided in the form of an arrangement in which the interface structure, such as bundle of hollow fibres, is held together by so-called potting. The hollow fibres provide gas passages from the gas inlet zone through the gas-blood interface to the gas exhaust zone. The potting is provided at the ends of the hollow fibres and provides two wall structures as boundaries for the blood passage. One wall is located at the inlet-facing side of the fibres, between the gas inlet zone and the gas-blood interface, and another wall at the outlet-facing side of the fibres, between the gas-blood interface and the gas exhaust zone. The area between the potting may be considered an interface chamber within which blood may pass around the hollow fibres, while oxygenation gas passes within the hollow fibres.

The supply gas is understood to be oxygenation gas, which is also referred to as "sweep" gas. The sweep gas is supplied to the oxygenator and initially reaches the gas inlet zone from where the gas can then pass into the many different openings of the hollow fibres that make up the gas-blood interface. The oxygenator may comprise one or more partition structures each dividing the gas inlet zone into a plurality of gas inlet sections, each section having a border with a different region of the gas-blood interface. The border can be imagined to correspond to an area of the potting in contact with the gas inlet zone. For instance, a partition structure may be a wall, located within the potting material between groups of hollow fibres, and extending from the potting material into the gas inlet zone such that each gas inlet section separated by the wall is fluidly connected to a different group of hollow fibres. The partitions allow each section to be supplied by supply gas of different flow rate and/or composition. Thereby, different gas transition conditions are provided for each section between the gas inlet zone and the interface chamber. This is in contrast to conventional fibre oxygenators which, although comprising multiple fibre passages, are not by design able to supply gas of different properties, and rather are designed to provide the same oxygenation gas to a common inlet chamber and therefore to each of the multiple fibre passages. Herein, a conventional oxygenator design is referred to a single-region oxygenator, and an oxygenator design with separately supplyable gas-blood interface regions is referred to as a multi-region oxygenator. A multi-region oxygenator may by supplied by different gas supply systems.

The present oxygenation gas supply control system allows a single set of hospital ports to be used to supply multiple gas inlet sections. As can be imagined, a hospital operating room may be equipped with certain supplies including an air supply port, an oxygen supply port, and other ports such as nitrogen, carbon dioxide, and suction (sub-atmospheric pressure) ports, whereas nitrogen is typically supplied as "air" i.e. a standardised mix of 21% oxygen and 79% nitrogen. Herein such a supply is referred to as "nitrogen" supply even though in many clinical settings the nitrogen would be expected to be supplied in the form of "air" including an oxygen fraction. The present invention addresses a situation in which there is only a limited number of ports, e.g. a single oxygen-supply port and a single air-supply port available for treatment use.

Particularly for a multi-region oxygenator, the present gas supply system may be used instead of multiple individual sweep gas blending units. By way of the invention, a single blending unit can be used to blend different streams of oxygenation gas to be supplied to multiple oxygenator gas inlets, with the possibility that each stream has different properties, to be provided, for instance, with different flow rates and/or with different composition.

In some embodiments, the gas supply control system is operable in a configuration blocking supply gas output through one or more of the gas output lines and maintaining supply gas output through at least one of the gas output lines.

This allows the gas supply control system to be used for different multi-region oxygenator designs. E.g., the gas supply control system may comprise a plurality of gas output lines, for instance three gas output lines. As such, the gas supply control system may be used to supply three different gas streams, one to each one of the three gas output lines. However, the same gas supply control system may also be used for a multi-region oxygenator with only two individually supplyable gas-blood interface regions, and in that example only two of the three gas output lines would need to be active. This allows the same type of gas supply control system to be installed or retrofitted with different oxygenator types. The configuration that blocks supply gas output may be provided as a physical device or by way of control logic such as software.

In some embodiments, the gas supply control system is operable in a configuration in which only one of the gas output lines is used to provide a supply gas output.

It will be understood that in a configuration in which only one of the gas output lines is supplied with the supply gas output, the other outlets are not supplying gas. In this configuration, the gas supply control system can be used like a supply system for a conventional single-region oxygenator, because only one gas output line of the plurality of gas output lines is used to supply gas to an oxygenator. This allows the present gas supply control system to be used both for multi-region oxygenator designs and for single region oxygenator designs.

This means the gas supply control system, in particular the same gas supply control system design, is suitable to be installed or retrofitted in an oxygenation system regardless of the oxygenator type used in it.

In some embodiments, the gas supply control system is further configured for connection to an external gas supply port to receive supplied carbon dioxide, wherein the gas supply control system is operable in a configuration allowing it to create a supply gas output comprising a predetermined portion of supplied carbon dioxide.

Typical oxygenation gas is blended from oxygen and nitrogen. The oxygen and nitrogen components may be provided in the form of air (providing a mix of about 21% oxygen and 79% nitrogen) and pure oxygen, for blending a composition with more than 21% oxygen. In certain clinical scenarios, particularly for paediatric patients, it may be necessary to blend carbon dioxide into the oxygenation gas.

Herein, a reference to a gas such as oxygen, nitrogen, air, or carbon dioxide is understood to mean the gas in the form supplied by a hospital and suitable for use with extracorporeal oxygenation. The supplied gas may not necessarily be a pure gas. For instance, the carbon dioxide may be supplied in the form of a carbogen gas mixture comprising oxygen and carbon dioxide. Such gas mixtures may be used to provide the hospital-supplied carbon dioxide.

In some embodiments, the gas supply control system is configured to blend supply gas with a predetermined portion of supplied carbon dioxide after blending supplied nitrogen and supplied oxygen.

This allows a mix of oxygen and nitrogen (air) to be blended to a desired degree of accuracy, providing an opportunity to monitor the blended amounts of nitrogen and oxygen, before blending a further component into the gas supply. To this end, the line feeding carbon dioxide into the gas mix may be connected downstream of the lines feeding oxygen and nitrogen (air).

In some embodiments, the gas supply control system is operable in a configuration allowing it to create the supply gas output using only, or practically only, supplied oxygen.

This allows the supply gas output to be constituted by oxygen with the degree of purity supplied by the hospital (herein for simplification referred to as 'pure oxygen'), or, of carbon dioxide is added, by a blend of oxygen and carbon dioxide. Effectively, the arrangement avoids the need to blend nitrogen (in the form of hospital-supplied air) into the supply gas output.

In some embodiments, the gas supply control system comprises a sensor arrangement allowing it to determine flow rates of the predetermined portion of supplied oxygen, the predetermined portion of supplied nitrogen, and of the supply gas output, wherein the gas supply control system comprises control logic allowing it to determine whether or not the flow rate of the supply gas output corresponds to a sum of the flow rate of the predetermined portion of supplied oxygen and of the flow rate of the predetermined portion of supplied nitrogen.

When the gas supply control system is set to provide a supply gas from multiple external gas supply ports, this allows a continuous monitoring if the supply gas output matches the amount of gases blended to a supply gas. In the event that the sums of the flow rates differ from the expected total, a warning protocol or other counteractive measures can be invoked. It will be understood that appropriate thresholds may be used to define safety margins, to reduce the likelihood of false positives.

In some embodiments, a sensor to determine the flow rate of the supply gas output is upstream of the feed for blending a predetermined portion of carbon dioxide into the configured to supply gas output.

Locating a flow sensor upstream of the carbon dioxide intake allows a flow measurement of the blended gas to be made while it is made up of fewer components.

In some embodiments, the gas supply control system comprises a sensor arrangement allowing it to determine flow rates of the predetermined portion of supplied oxygen, and of the supply gas output through each gas output line, wherein the gas supply control system comprises control logic allowing it to determine whether or not the flow rate of the predetermined portion of the supplied oxygen corresponds to a sum of the flow rates through each gas output line.

This allows a continuous monitoring whether or not the supply gas output through several gas output lines corresponds to the supply gas directed towards the outlets. In the event that the sums of the flow rates differ from the expected total, a warning protocol or other counteractive measures can be invoked. It will be understood that appropriate thresholds may be used to define safety margins, to reduce the likelihood of false positives.

In some embodiments, the gas supply control system control comprises a configuration allowing it to switch between a mixed-gas supply mode and a high-oxygen supply mode, wherein in the mixed-gas supply mode the gas output is created from supplied oxygen and supplied nitrogen and wherein in the high-oxygen supply mode the gas output is created from supplied oxygen. The high-oxygen mode can be defined as a mode in which the gas output comprises less nitrogen than in the mixed-gas supply mode. In the high-oxygen supply mode, the gas output can be created without nitrogen, i.e. without blending in any practically relevant amount of supplied nitrogen.

This allows the gas supply control system to be used for different oxygenator designs, such as oxygenators that are designed for use with sweep gas comprising oxygen and nitrogen, and oxygenators that are designed for use with high-oxygen content gas.

By high oxygen content, as may be supplied in a high-oxygen supply mode, a supply gas oxygen content is meant that in conventional oxygenator designs would create a greater high risk of hyperoxia. The supply gas oxygen content may be defined as over 60%, over 70%, over 80%, over 90%, or over 95% (v/v) oxygen. The present invention provides the option of using sweep gas with an oxygen content defined by the hospital oxygen supply gas, which may be practically pure oxygen, optionally blended with a carbon dioxide fraction.

In some embodiments, the gas supply control system is operable to supply a first number of gas output lines in the mixed-gas supply mode and to supply a second number that differs from the first number of gas output lines in the high-oxygen supply mode.

In some embodiments, the gas supply control system is operable to supply one gas output line in the mixed-gas supply mode and to supply each gas output line in the high-oxygen supply mode.

In the high-oxygen supply mode, each gas output line may be used to supply a gas output to the oxygenator. In the high-oxygen supply mode, not every gas output line needs to be active. For instance, also in the high-oxygen supply mode only one of two gas output lines may be active to supply gas to an oxygenator. However, in the high-oxygen supply mode the gas supply control system is operable to activate and modulate two or more gas output lines. The control of the gas output may be operated by control logic, which may be embodied in software.

Underlying the development of this feature is the appreciation that a multi-region oxygenator can likely be operated by using pure oxygen as supply gas output to each gas-blood interface region to be supplied. In other words, it is not necessarily a requirement to supply a blend of air and oxygen to a multi-region oxygenator. Instead, oxygen practically without nitrogen (i.e. pure oxygen unless blended with carbon dioxide) is supplied at different flow rates to the different gas-blood interface regions, and pure oxygen may be supplied to only some of the gas-blood interface regions during different phases of a procedure. This provides a good degree of control over the oxygenation. A risk of supplying too high a degree of oxygen (hyperoxia) can be avoided by supplying oxygen at a lower flow rate, or no oxygen, to some of the gas-blood interface regions. This is briefly illustrated using an example of a two-region oxygenator supplied with oxygen by the gas supply control system operating in the high-oxygen supply mode. In that case, the oxygenator would be configured to supply each of the two regions with oxygenation gas. One interface region of the oxygenator may be continuously supplied with oxygen via one gas output line. Another interface region of the oxygenator may be intermittently supplied with oxygen supplied via another gas output line.

In some embodiments, the gas supply control system comprises a gas pressure sensor arrangement, wherein each of the gas output lines comprises an individual output pressure sensor and a vent individually actuatable in the event of an adverse pressure measurement in the respective gas output line.

In accordance with a second aspect of the invention there is provided a gas extraction system.

The gas extraction system is for an extracorporeal ventilation system comprising an exhaust gas removal line for connection to external exhaust suction port to be provided. The gas extraction system further comprises a sampling line and a connection merging the sampling line and the exhaust gas removal line to allow suction from the exhaust suction port to be applied to the sampling line. The sampling line comprises an outlet port for passively venting when not connected to the exhaust suction port.

It will be understood that the exhaust gas removal line is configured for connection to an exhaust gas suction source as is usually provided as part of hospital infrastructure. By exhaust gas suction source, a low-pressure port (also referred to as 'hospital vacuum') is meant that may operate at a defined pressure below atmospheric pressure, such as at 0.5 atm. It will be understood that the exhaust gas removal line is operable to withdraw exhaust gas from the oxygenator via the exhaust port when connected to the exhaust gas suction source. In certain settings, a different type of suction source may be provided.

The exhaust gas may comprise anaesthesia gas. In that case, releasing the exhaust gas into the atmosphere is undesirable and so hospitals may require compliance with a specific exhaust gas collection protocol, i.e. the exhaust gas suction source may collect exhaust gases into a specific treatment chamber or collection chamber.

This can provide conflicting exhaust gas flow requirements if it is desired to analyse certain properties of the exhaust gas, e.g. by continuous or intermittent sensor measurement. By providing a separate sampling line, the flow conditions in the sampling line can be arranged differently to the exhaust line. However, exhaust gas sampled for analysis may still need to be treated in the same manner as other exhaust gas. By merging the sampling line into the exhaust gas removal line, the same exhaust suction port can be used for both the exhaust gas removal line and the sampling line.

In some embodiments, the gas extraction system comprises a flow restrictor for the sampling line allowing the flow rate in at least a portion of the sampling line to be reduced relative to the exhaust line when suction from the exhaust suction port is applied to it.

The flow restrictor may also have the effect of practically creating atmospheric conditions in the portion of the sampling line despite the application of suction from the exhaust suction port.

The flow restrictor may be a device as simple as an orifice plate. By using a suitably dimensioned flow restrictor, the flow rate in the portion of the sampling line may be reduced to no more than is required to induce flow. This allows a better control over the flow conditions in the sampling line, compared to relatively stronger flow rates than may otherwise be present if the sampling line is connected directly to a hospital exhaust suction port.

In some embodiments, the gas extraction system comprises a sensor arrangement in the portion with reduced flow.

The sensor arrangement may comprise an oxygen sensor, a carbon dioxide sensor, an anaesthesia sensor, and/or other sensors to obtain measurements from the exhaust gas.

In some embodiments, the gas extraction system comprises an assisted venous drainage line for connection to a drainage suction port.

In some embodiments, the connection of the drainage suction port to the assisted venous drainage line is isolated from the exhaust gas removal line.

This allows different suction-induced pressure conditions to be provided particularly in clinical scenarios in which there is no requirement to collect exhaust gas. In that case, connecting both the exhaust gas removal line and a vacuum assisted venous drainage may create flow conditions in the exhaust line that are difficult to control, due to a relatively higher suction pressure in the venous drainage subsystem. In that case, it is an advantage to be able to operate vacuum assisted venous drainage and exhaust removal independently.

In some embodiments, the gas extraction system comprises control logic and flow control configuration allowing it to modulate the suction flow rate of the drainage line differently from the suction flow rate of the exhaust gas removal line.

In some embodiments, the gas extraction system comprises control logic and pressure control configuration allowing it to modulate the suction pressure of the drainage line differently from the suction pressure of the exhaust gas removal line.

An arrangement allowing the waste gas removal line to be operated at different flow rates than other suction lines provides the opportunity to react to different flow demands. For instance, in certain clinical scenarios it may be preferable to operate the exhaust line with a higher flow rate but close to atmospheric pressure, whereas the venous drainage line may have to be operated at a lower sub-atmospheric pressure.

In accordance with a further aspect of the present invention, there is provided an extracorporeal oxygenation system comprising a gas supply control system in accordance with the first aspect and an oxygenator, wherein the oxygenator comprises a single sweep gas inlet, and wherein one of the gas output lines is connected to the sweep gas inlet and the oxygenation gas supply control system is configured to supply the one gas output line with a supply gas output.

In accordance with a further aspect of the present invention, there is provided an extracorporeal oxygenation system comprising a gas supply control system in accordance with the first aspect and an oxygenator, wherein the oxygenator comprises a plurality of sweep gas inlets, and wherein each of the sweep gas inlets is connected to a gas output line of the gas supply control system.

In some embodiments of each of the further aspects, the extracorporeal oxygenation system comprises a gas extraction system according to the second aspect.

By way of a control system, the exhaust gas flow rates can be modulated relative to the total amount of sweep gas provided to the oxygenator, for instance if it is desired to maintain the exhaust flow rate above the total sweep gas supply rate. This allows a single exhaust collection to be used for a multi-region oxygenator.

The present arrangement provides another mechanism for altering gas properties by being able to modulate the gas composition, flow rates, and/or regions of the gas-blood interface to be utilised in order to maintain a blood property at a set point. By maintaining a property, it is meant that the system is responsive to compensate gas parameters for temporary fluctuations.

DESCRIPTION OF THE FIGURES

Exemplary embodiments of the invention will now be described with reference to the Figures, in which.

DESCRIPTION

Figure 1:
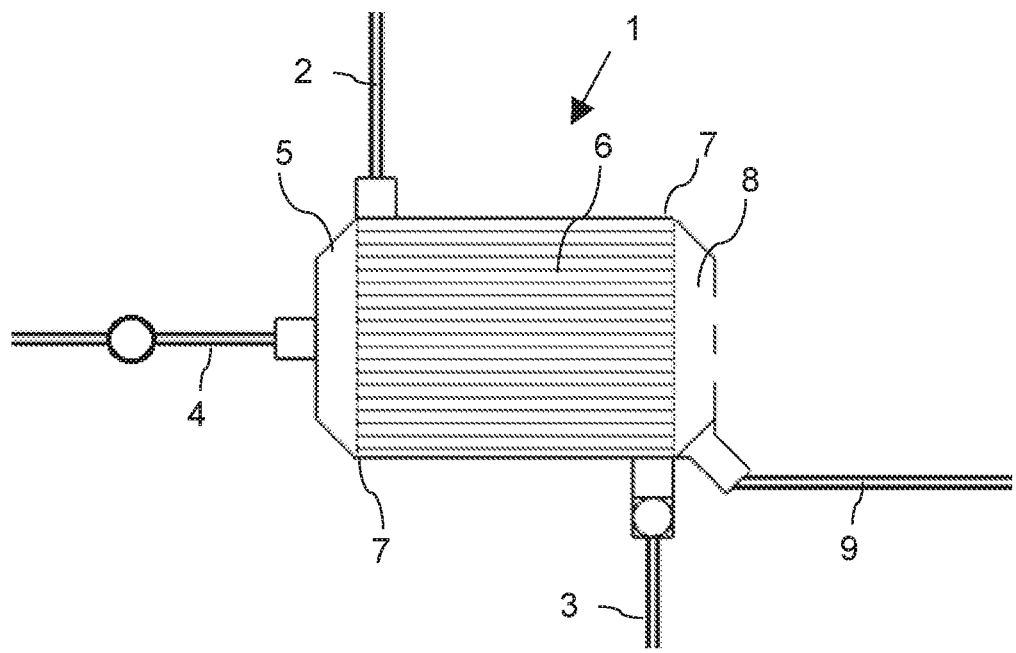
FIG. 1 shows features of a conventional oxygenator arrangement for use with the present gas supply control system.

FIG. 1 shows elements expected to be found in a known oxygenator 1 used in extracorporeal ventilation. The oxygenator 1 is provided to expose oxygen-reduced, or venous, blood to a gas supply comprising oxygen thereby to allow a gas exchange between the blood and the gas supply in which the blood is oxygenated and carbon dioxide is removed in order to provide oxygen-enriched arterial blood. The oxygenator 1 comprises a blood passage comprising blood inlet 2 via which venous blood is supplied into the oxygenator 1 and a blood outlet 3 via which outgoing blood leaves the oxygenator 1 for further use, often as arterial blood to be returned to a patient. The oxygenator 1 also comprises a gas passage comprising a sweep gas supply 4 leading via an inlet chamber 5 through a gas-blood interface 7 and via an exhaust chamber 8 to an exhaust passage 9. The gas supply control system of the present invention (not shown in FIG. 1) would be connected upstream of the oxygenator 1 to provide supply gas to the sweep gas supply 4.

Modern gas-blood interfaces typically comprise a bundle of several thousand hollow, micro-porous fibres with micro-porous, gas-permeable properties. The sweep gas is supplied through the interior, hollow space of the fibres and blood flows around the fibres and gas exchange is promoted by relative diffusion gradients between the concentrations of oxygen and carbon dioxide in blood and gas, respectively. The hollow fibres are held together at their ends by so-called potting 7 which seals off the blood passage from the inlet chamber 5 and the exhaust chamber 8.

The aim of such an oxygenator type is to modulate the partial pressure of oxygen PaO2 in the outgoing blood. The aim may also be to modulate the partial pressure of carbon dioxide PaCO2 in the outgoing blood. PaO2 may be modulated by adjusting the oxygen percentage (ie partial oxygen pressure) of the oxygenation gas, the remaining component being, conventionally, mainly nitrogen. PaCO2 may be modulated by adjusting the flow rate of the oxygenation gas. Using an oxygenation gas supply system such as described in WO2016/087859 and WO2016087861 by the present applicant, both the composition and the flow rate of the oxygenation gas can be controlled simultaneously, allowing both the PaO2 and PaCO2 that is expected in the outgoing blood to be modulated simultaneously.

Figure 2:
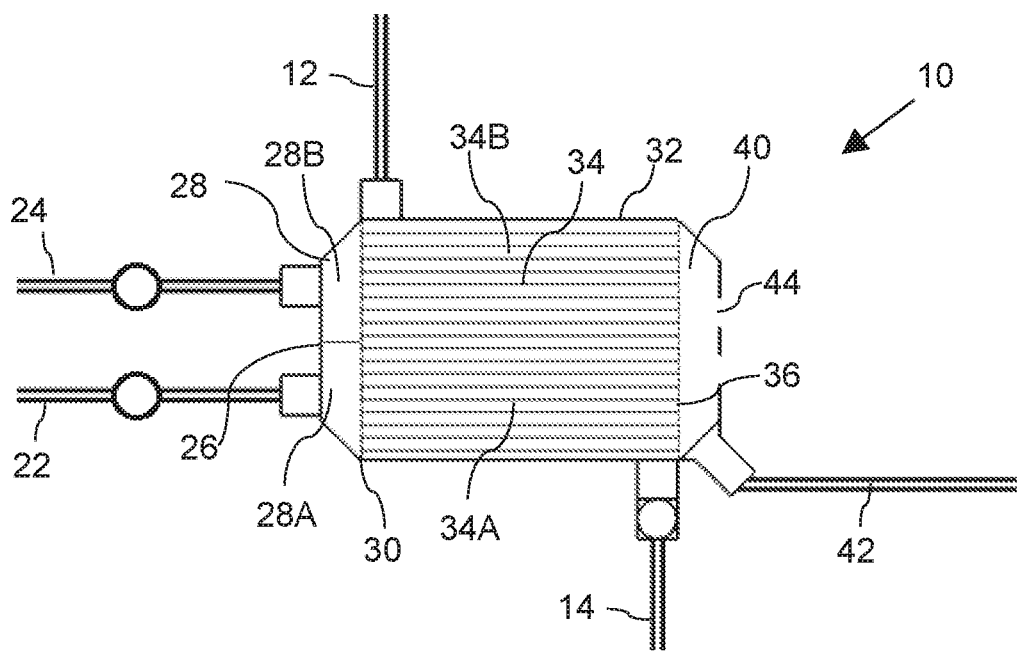
FIG. 2 shows features of a multi-region oxygenator for use with the present gas supply control system.

FIG. 2 shows an oxygenator 10 described in more detail in International Patent Application No PCT/GB2019/050579 that may be used with, or in, embodiments of the invention. The oxygenator 10 comprises a blood inlet 12 and a blood outlet 14 providing a blood passage through the oxygenator 10. The oxygenator 10 comprises connections for a first sweep gas supply 22 and a second sweep gas supply 24. The gas supply control system of the present invention (not shown in FIG. 2) would be connected upstream of the oxygenator 10 to supply the first and second sweep gas supplies 22 and 24.

The first and second sweep gas supplies 22 and 24 lead into a gas inlet zone 28 of the housing. The gas inlet zone 28 is fluidly connected with a gas-blood interface 32, which comprises a plurality of hollow fibres 34. The oxygenator 10 may also be referred to as a membrane oxygenator. The hollow fibres 34 are gathered at the gas inlet end by inlet-facing potting 30 constituting a gas interface border and at the gas exhaust end by outlet-facing potting 36. The gas passage leads from the gas inlet zone 28 via the hollow fibres 34 to an exhaust zone 40 downstream of the gas-blood interface 32 from where an exhaust gas line 42 extracts the gas. The oxygenator 10 comprises a housing that is gas tight at the gas inlet zone 28, to avoid contamination of the oxygenation gas. At the other end, at the exhaust zone 40, the housing comprises several openings 44 to allow pressure equilibration with the environment, in order to avoid a pressure build-up within the gas-blood interface 32. The blood passage between the blood inlet 12 and the blood outlet 14 is provided by the gas-blood interface 32 bounded by the inlet-facing potting 30 and the outlet-facing potting 36, and constituted by the volume outside the hollow fibres 34. The area between the potting 30 and 36 provides a gas-blood interface chamber.

Within the gas inlet zone 28 the oxygenator 10 comprises a partition 26 that at least partially separates the gas inlet zone into two compartments, a first gas inlet compartment 28A and a second gas inlet compartment 28B, each compartment constituting a section of the gas inlet zone. Each gas inlet compartment 28A, 28B can be considered as adjoining a different portion of the inlet-facing potting 30. As such, each gas inlet compartment has a different border with the gas-blood interface 32.

Some hollow fibre bundles connect into the first gas inlet compartment 28A and are supplyable by gas from the first gas inlet compartment 28A, i.e. via the first sweep gas supply 22. These hollow fibres are illustrated in FIG. 2 as first group of hollow fibres 34A. Likewise, a set of second group of hollow fibres 34B is fluidly connected with the second gas inlet compartment 28B, i.e. supplyable via the second sweep gas supply 24.

The partition 26 is illustrated in a fixed position in FIG. 2. The partition 26 may be fixed in position, e.g. according to an oxygenator moulding design. The partition 26 may be re-positionable at different locations.

The present invention is concerned with a gas supply control system capable of providing oxygenation gas to a plurality of sweep gas supplies, such as a first sweep gas supply 22 and a second sweep gas supply 24.

Figure 3:
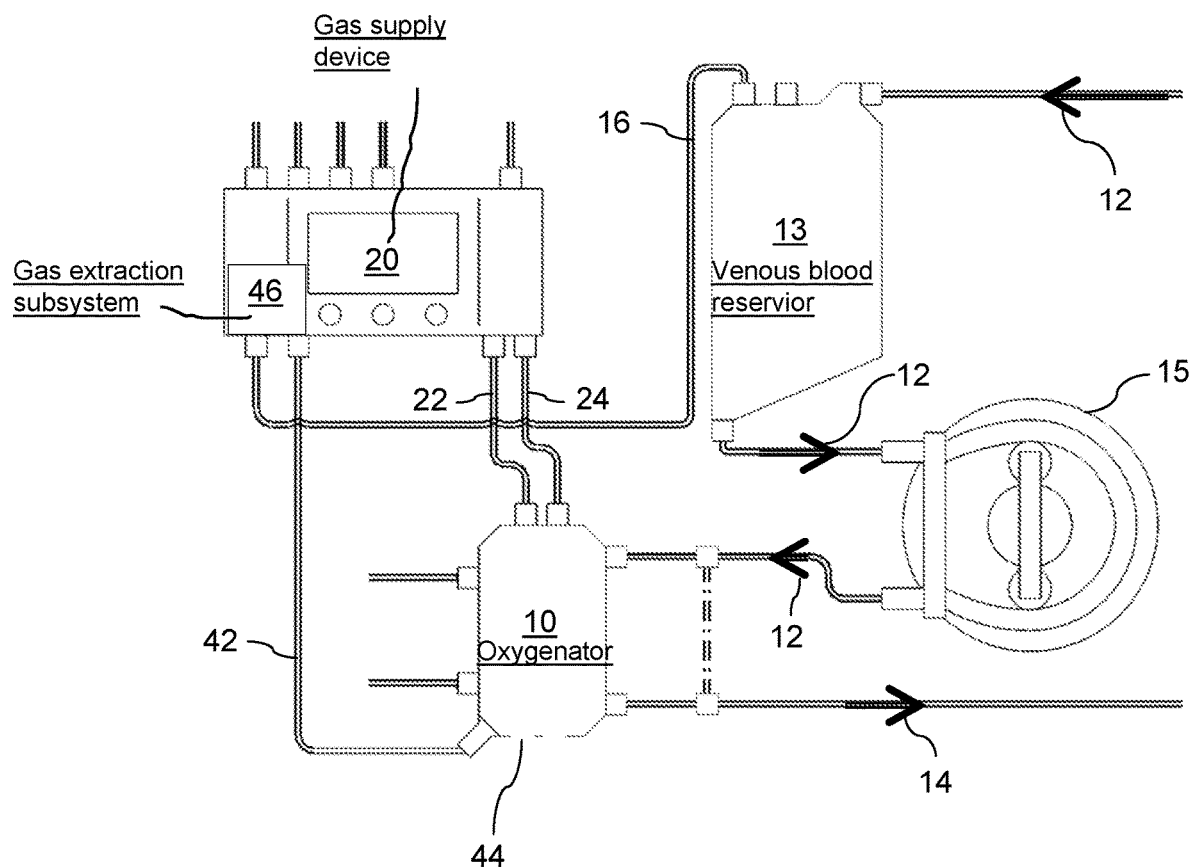
FIG. 3 is a schematic illustration of an extracorporeal perfusion system comprising an embodiment.

FIG. 3 illustrates an extracorporeal perfusion system comprising the oxygenator 10. In FIG. 3, no hollow fibres are indicated inside the oxygenator 10, to simplify the illustration, and some connections (blood inlet 12 and blood outlet 14) are positioned differently, but it will be understood that the oxygenator 10 of FIGS. 2 and 3 can be identical. Likewise, other oxygenator embodiments of the invention may be used with the extracorporeal perfusion system. Venous blood flows via a blood inlet 12 into a venous blood reservoir 13 from where the blood is pumped via a pump 15 towards the oxygenator 10. The venous blood may change in condition when passing the blood reservoir 13 and the pump 15, and may be provided with blood treatment agents. For the purposes of the present specification, the venous blood is blood intended to be provided to the oxygenator 10 in order to be oxygenated and to have its carbon dioxide content reduced. In the oxygenator 10, the blood is exposed to oxygenation gas and exits via the blood outlet 14. A gas supply control system 20 is configured to supply oxygenation gas via a first sweep gas supply 22 towards the oxygenator 10. FIG. 3 also shows a second sweep gas supply 24 to provide oxygenation gas to the oxygenator 10. After the gas exchange, gas leaves the oxygenator 10 via the exhaust gas line 42. The exhaust gas flow is controlled by a gas extraction subsystem 46, which may be connected to one or more low-pressure source connections. The low-pressure source creates an exhaust gas flow sufficient to promote a flow from the gas inlet zone 28 to the exhaust zone 40. Although not illustrated in FIG. 3, the exhaust gas line 42 may lead to an exhaust gas collection unit to prevent distribution of anaesthetic gas.

For practical purposes, when assessing the oxygenator gas-blood exchange dynamics, the flow-inducing pressure gradient is usually considered negligible and often the pressure profile across the oxygenator 10 is considered constant as much as practically achievable. The pressure in which the oxygenator 10 operates is atmospheric, particularly as the housing of the oxygenator 10 at the exhaust side comprises openings 44 providing auxiliary vents. For the purposes of the present description in relation to oxygenator 10, incoming blood is provided via the blood inlet 12 towards the oxygenator 10, and outgoing blood is removed from the oxygenator via the blood outlet 14. Collection of venous blood into the venous blood reservoir 13 is assisted by application of suction, or 'vacuum' via a vacuum-assisted venous drainage line 16 connected to the gas extraction subsystem 46. Although the venous drainage line 16 and the exhaust gas line 42 are illustrated as being connected to the same gas extraction subsystem 46, these may be connected to different suction control systems. Also, although only a single exhaust gas line connection is depicted in FIG. 2, of the oxygenator regions (groups of hollow fibres) may be connected to a separate exhaust line. In that case, each exhaust line may be operated individually, with an individual exhaust flow control, or multiple exhaust line may be operated by a common exhaust control.

The oxygenation arrangement described in FIGS. 2 and 3 allows an oxygen content in the oxygenation gas to be used that is much higher than 21%, even close to 100% or practically pure oxygen, even at normal atmospheric pressure conditions, while avoiding that all fibre regions of the oxygenator are exposed to pure oxygen, or otherwise unsafely high levels of oxygen, thereby providing a mechanism to reduce the occurrence of, and practically avoid, hyperoxia. This allows nitrogen in the oxygenation gas to be practically avoided.

The present invention is based on the appreciation that use of oxygenation gas without, or a lower, nitrogen content favours the removal of nitrogen from the blood, while still allowing a controlled oxygenation and carbon dioxide removal.

This may be achieved, as set out in International Patent Application No PCT/GB2019/050579 and in FIGS. 2 and 3 illustrated herein, by passing the oxygenation gas, which may be up to 100% oxygen, through only a portion of the hollow fibres, e.g. through only the first group of fibres 34A, whereas less (lower flow rate of pure oxygen) or no oxygen is fed through the second group of fibres 34B. The practical effect of operating the arrangement in this manner is that the sweep-gas exposed area of the gas-blood interface is modulatable during operation of the oxygenator. Blood passes in a practically continuous flow via lesser oxygenated, or non-oxygenated, hollow fibres (e.g., the second group of fibres 34B indicated in FIG. 2) before it passes the oxygenated hollow fibres (e.g., the first group of fibres 34A). For instance, using an arrangement and operation mode such as that described in FIG. 2, in FIG. 2 blood is allowed to flow in a practically continuous manner into the oxygenator 10 from the upper part of the oxygenator past the second group of hollow fibres 34B before passing the first group of hollow fibres 34A and before exiting via the blood outlet 14. Where the blood passes through these two areas of fibres, whether or not ventilated, gas exchange takes place. By using different oxygenation gas flow rates for the first and second groups of hollow fibres 34A and 34B, and/or different oxygenation gas composition, different oxygen gradients and total gas gradients can be achieved. The flow rates through the first and second groups of hollow fibres 34A and 34B influence the carbon dioxide removal rates.

In the illustrated example, by limiting the total area of hollow fibres that are actively ventilated (e.g. by providing oxygenation gas only to the first group of fibres 34A instead of both the first and second group of fibres 34A and 34B), the oxygenation uptake of the blood can be influenced, and the gas flow rate provides control of carbon dioxide removal rates.

In known oxygenator designs such as the FIG. 1 arrangement, the oxygenation rate is controlled by modulating the composition, mainly the ratio of oxygen to nitrogen (air), of the oxygenation gas, wherein care has to be taken not to induce hyperoxia (too much oxygen) to the point that is considered potentially detrimental. For instance, a continuous supply over time of pure oxygen in a conventional oxygenator design is very likely to cause hyperoxia at detrimental levels. In the arrangement described in FIGS. 2 and 3, the oxygenation rate can be influenced by supplying, or not supplying, oxygenation gas through the second group of hollow fibres 34B, while using higher oxygen content, even 100% oxygen. It is also an option to modulate the oxygenation gas composition by adding carbon dioxide, or a carbogen gas mixture, but it is not necessary to use nitrogen in the oxygenation gas in order to provide a lower partial pressure of oxygen in the oxygenation gas. As such, with a lower nitrogen partial pressure of the gas supplied, or with negligible amounts of nitrogen supplied to the gas-blood interface, it is possible to achieve a better removal rate of dissolved nitrogen from the blood over time.

An estimated oxygen transfer rate can be calculated based on factors including, but not necessarily limited to, a patient's size, metabolic demand, and blood flow rate. If the estimated oxygen transfer rate is greater than the maximum oxygen transfer rate that can be achieved by a maximum gas flow of pure oxygen via the first sweep gas supply, the multi-region design of the oxygenator 10 allows additional gas to be supplied to the second group of hollow fibres 34B. The gas flow rates of the first and second sweep gas supply 22 and/or 24, respectively, can be modulated to achieve the desired carbon dioxide removal rate.

For example, while no oxygenation gas is supplied to the second group of hollow fibres 34B, venous blood, which has the lowest total partial pressures of gases in the blood due to the low oxygen partial pressure, is allowed to interact with the hollow fibres of the second group of hollow fibres 34B. In one example, with no, or practically no gas flowing through the second hollow fibre membranes 34B, gaseous microemboli (GME) present in the venous blood experience pressure gradient conditions that encourage their removal. The removal of GME occurs due to the gradient between the GME and the inside of the hollow fibres, as well as the physical pressure applied by the blood on the GME bubble as that bubble is pushed past the surfaces the hollow fibres. The blood may therefore contain a significantly reduced number of GME after passing through the second group of hollow fibres 34B prior to reaching the first group of hollow fibres 34A. When the blood passes the first group of hollow fibres 34A, as these are supplied with a high or pure oxygen content, the blood is oxygenated with a steeper oxygen partial pressure gradient. At the same time, the oxygenation gas, to the extent that it does not comprise a higher nitrogen partial pressure than the blood, does not promote the formation of GME.

In the described exemplary use of the arrangement, the opportunity for oxygenating the blood is in one mode of operation limited to the blood passing the first group of hollow fibres 34A. If the resultant blood oxygen pressure is not high enough, the present arrangement allows additional oxygenation gas to be supplied to the second group of hollow fibres 34B. The gas supply may be gradually increased. Likewise, the opportunity for removing carbon dioxide is a function of the total gas flow. If, in the described example, the carbon dioxide removal rate is insufficient despite maximal gas flow through the first group of hollow fibres 34A, the present arrangement allows additional oxygenation gas to be supplied to the second group of hollow fibres 34B. The composition and/or the flow rate of the second sweep gas supply may be different from that of the first sweep gas supply.

If a high oxygen content, or pure oxygen, is used for both groups of hollow fibres, and if a carbon-dioxide removal demand requires high flow rates through both membranes, this may result in a higher oxygenation value than the ideal oxygen target value. However, even if too high an oxygenation value is generated, this would be a temporary issue. The present arrangement allows a nitrogen partial pressure to be avoided while reducing the occurrence of hyperoxia conditions to less than would otherwise be the case if 100% oxygen was used as oxygenation gas for an entire oxygenator.

Figure 4:
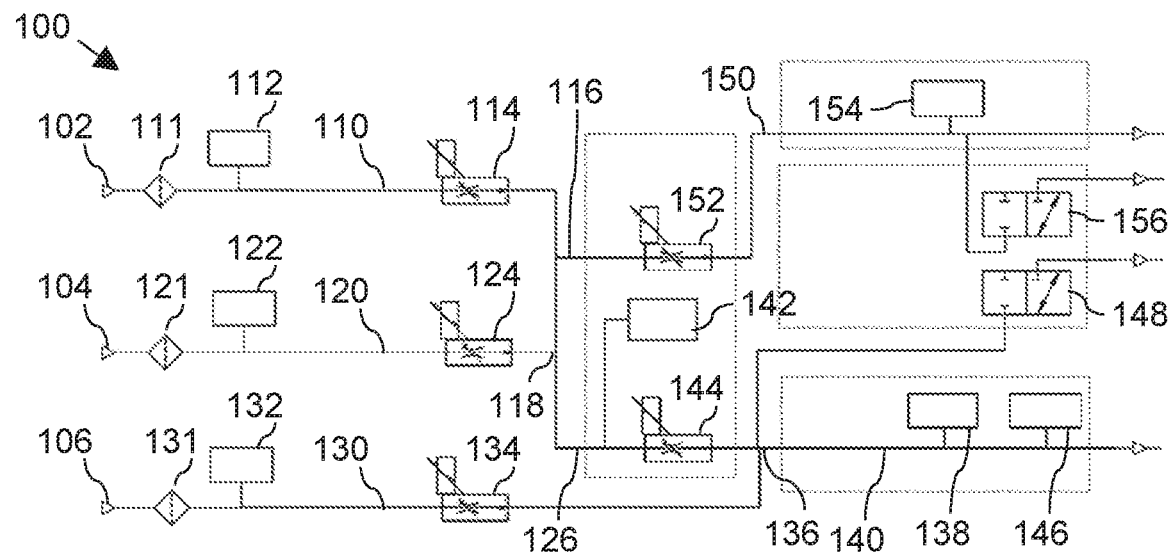
FIG. 4 shows a schematic diagram of a gas supply control system in accordance with the present disclosure.

FIG. 4 shows, schematically, the layout of a gas supply control system 100 in accordance with the invention. The components of the control system 100 may be provided as a gas supply device 20 (see FIG. 3), e.g. in a single housing, although it is understood that certain elements of the control system such as control logic may be located and/or executed in a different device.

The gas supply device 20 comprises three gas source connections 102, 104 and 106. A first gas source connection 102 is configured for connection to a hospital oxygen port. The hospital oxygen port can be assumed to supply practically pure oxygen. A second gas source connection 104 is configured for connection to a hospital air supply port. The hospital air supply port can be assumed to supply air, i.e. a composition comprising typically 21% oxygen and 79% nitrogen, but may also be any hospital gas usually provided for blending with oxygen, e.g. nitrogen. A third gas source connection 106 is configured for connection to a hospital carbon dioxide port, which may also be any hospital gas usually provided for blending in carbon dioxide, e.g. a carbogen mix comprising oxygen and carbon dioxide.

The oxygen, air (nitrogen) and carbon dioxide supplies are of a purity and sterility suitable for blending as an oxygenation gas. In this regard, an "air" mix is typically provided instead of pure nitrogen, but it will be understood that a reference herein to an air supply could cover a nitrogen gas supply. Carbon dioxide may be provided as pure gas or as mix, e.g. a carbogen gas mixture comprising oxygen and carbon dioxide. Conventionally, the oxygen and air supplies are to be blended to provide a supply gas output with a higher percentage oxygen than air, the remainder being mostly nitrogen.

The first gas source connection 102 supplies an oxygen intake line 110 comprising a first filter 111, an oxygen pressure sensor 112 and an oxygen mass flow controller 114. Downstream of the oxygen mass flow controller 114 is a first oxygen supply offtake 116 supplying a second gas outlet line 150. The first oxygen supply offtake 116 may be open to supply the second gas output line 150, or may be closed to shut supply via the second gas outlet line 150.

The second gas source connection 104 supplies an air intake line 120 comprising a second filter 121, an air pressure sensor 122 and an air mass flow controller 124. The third gas source connection 106 supplies a carbon dioxide intake line 130 comprising a third filter 131, a CO2 pressure sensor 132 and a CO2 mass flow controller 134.

Downstream of the air mass flow controller 124, the air intake line 120 merges with the oxygen intake line 110 at an oxygen-air junction 118, (which could also be referred to as oxygen-nitrogen junction). The oxygen-air junction 118 may be constituted by a blending chamber. The oxygen-air junction 118 may be upstream of a blending chamber (not illustrated in FIG. 4). Embodiments may not require a blending chamber, particularly if the flow rates and pressures of the air supply and oxygen supply have magnitudes that allow sufficient blending to be ensured.

Downstream of oxygen-air the junction 118, whether with or without blending chamber, the gas is blended and transported in a blended gas section 126 of the first gas output line 140. The first gas output line 140 comprises a first output pressure sensor 142 and a first output mass flow controller 144.

Downstream of the first output mass flow controller 144, the carbon dioxide intake line 130 merges via a CO2-mix junction 136 into the first gas output line 140. Downstream of the CO2-mix junction 136, the first gas output line 140 comprises a CO2 sensor 138 and a first output pressure sensor 146. If the fraction of CO2 is expected to be small relative to the fraction of oxygen and nitrogen, flow rate measurements may not provide a high degree of accuracy. In that case, it is an option that the CO2 sensor 138 measures the composition of the gas passing through the first gas output line 140, i.e. the percentage of carbon dioxide of the output gas through the first gas outlet line 140.

If required, the measurement can be corrected for the amount of oxygen and nitrogen in the gas passing through the first gas outlet line 140, because these values are known from the mass flow controllers upstream. This allows a wider range of sensors to be used for measuring CO2, including sensors that might otherwise not be suitable due to cross-correlation issues. A takeoff of the first gas output line 140 leads to a first vent 148 for venting excess gas from the first gas output line 140 if required.

The second gas output line 150 comprises a second output mass flow controller 152, a second output pressure sensor 154 and a takeoff leading to a second vent 156 for venting excess gas from the second gas output line 150 if required.

Carbon dioxide may be blended into the supply gas, if required, via the carbon dioxide intake line 130 and CO2-mix junction 136. As an illustrative example, carbon dioxide may be required to assist with blood acidity levels and blood gas solubility particularly in paediatric patients undergoing temperature changes, where the usual transition time of blood through the oxygenator is not sufficiently long to achieve a desired partial pressure of carbon dioxide in the outgoing blood, unless the oxygenation gas comprises a higher fraction of carbon dioxide.

As shown in FIG. 4, carbon dioxide is fed into the blended mix downstream of the first output mass flow controller at the CO2-/mix junction 136. Even though in a typical supply gas mix the portion of oxygen and air is considerably larger than that of carbon dioxide, the present arrangement allows the first output mass flow controller 144 to be used as a first-level indication that the flow rates of oxygen and air, if blended, are as expected, without having to consider an influence from the carbon dioxide feed (however small an amount this may be).

The components of the gas supply control system 100 can be operated in several modes. Below, a more detailed description of two modes, a mixed-gas supply mode and a high-oxygen supply mode are described in more detail.

Figure 5:
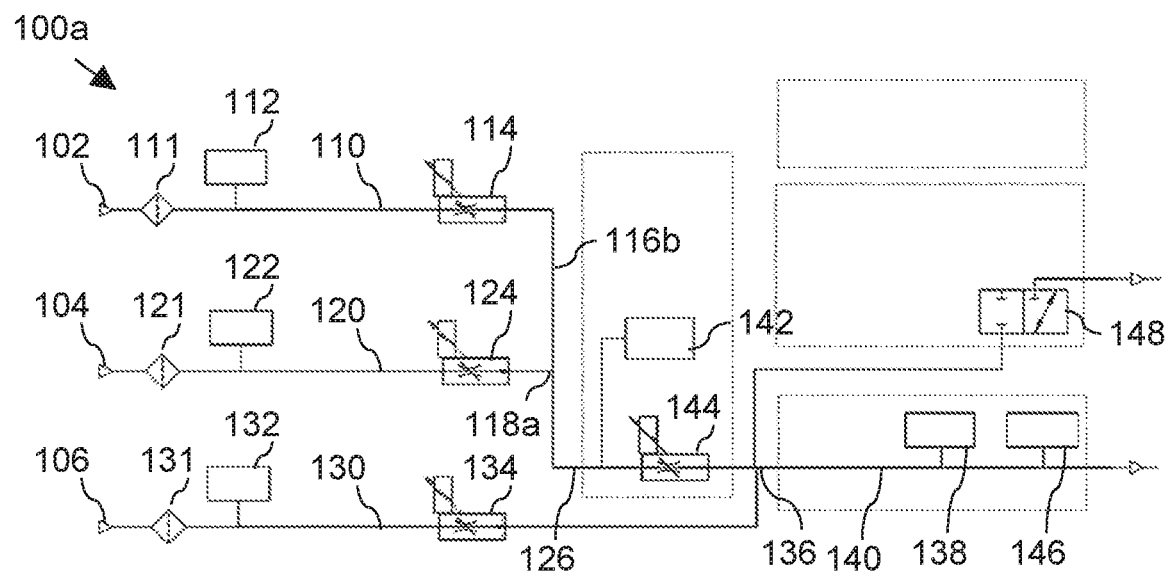
FIG. 5 illustrates active supply lines of the FIG. 5 control system in one mode of operation.

FIG. 5 shows the schematic of FIG. 4 in which the gas supply control system 100 is operated in a mixed-gas supply mode 100a. The first oxygen supply offtake 116 is shut, i.e. in a closed condition 116b, and no gas is supplied via the second gas output line 150. It will be understood that the example of a closable offtake is provided for illustrative purposes and any other suitable mechanism may be used to prevent flow through the second gas output line 150. To illustrate this mode, the second gas output line 150 is omitted from FIG. 5. In this configuration, the gas supply control system provides supply gas output via the first gas output line 140. In FIG. 5, the same numerals are used for equivalent components as in FIG. 4 without repeating their description.

In the mixed-gas supply mode 100a, the oxygen mass flow controller 114 is operated to provide a predetermined portion of oxygen for the mixed gas. The air mass flow controller 124 is operated to provide a predetermined portion of air for the mixed gas. After the oxygen-air junction 118, which is in an open condition 118a, the two predetermined portions of supplied oxygen and supplied air are blended, wherein blending may take place in a blending chamber (not shown) and flow along the blended gas section 126 towards the first gas output line 140.

The first output mass flow controller 144 allows the flow rate of the blended gas, i.e. the cumulative flow of the predetermined portions of oxygen and air, to be measured.

It will be understood that the flow rate through the first output mass flow controller 144 is expected to correspond to the sum of the flow rates passing through the oxygen mass flow controller 114 and the air mass flow controller 124. This provides an opportunity for the gas supply control system 100 to incorporate a safety check in which control logic determines whether there is a deviation from the expected flow rate.

If carbon dioxide is required in the supply gas output, this can be introduced via the carbon dioxide intake line 130 in the manner described in relation to FIG. 4 above.

Figure 6:
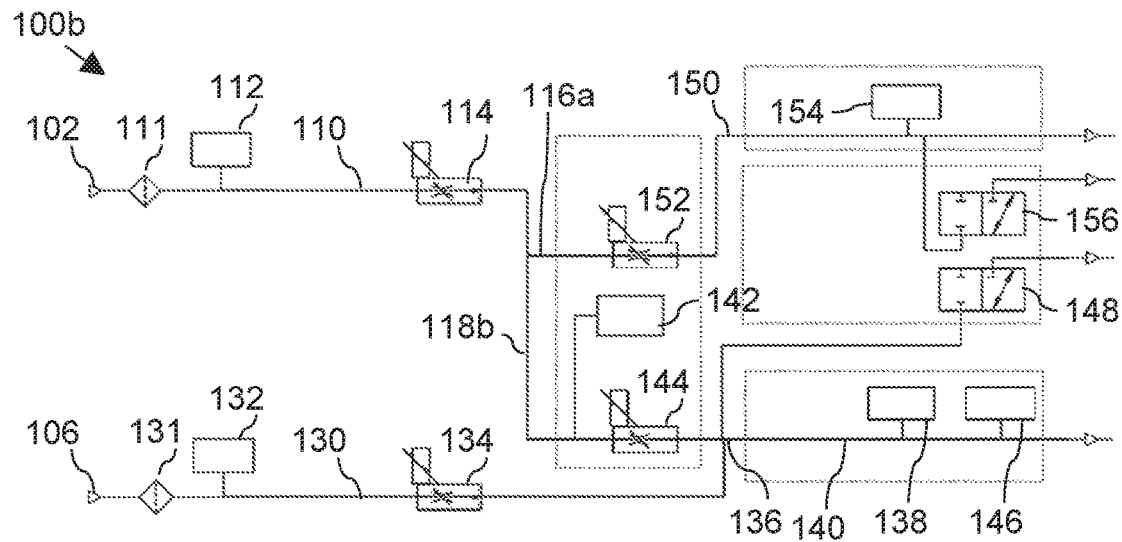
FIG. 6 illustrates active supply lines of the FIG. 5 control system in another mode of operation.

FIG. 6 shows the schematic of FIG. 4 in which the gas supply control system 100 is operated in a high-oxygen supply mode 100b. The first oxygen supply offtake 116 is in an open condition 116a to supply the second gas output line 150. In this configuration, the gas supply control system provides supply gas output via both the first gas output line 140 and the second gas output line 150. In FIG. 6, the same numerals are used for equivalent components as in FIG. 4 without repeating their description. This mode does not rely on mixing of nitrogen into the output gas, which means that no nitrogen needs to be blended into the gas output via the air intake line 120. As such, the supply gas output comprises a lower fraction of nitrogen (i.e. practically no nitrogen) in the high-oxygen supply mode than in the mixed-gas supply mode. In other words, the predetermined portion of supplied nitrogen may be zero. To illustrate this mode, the air intake line 120 is omitted from FIG. 6, and the oxygen-air junction 118 is indicated in a linear condition 118b whereby it provides a passage from the oxygen intake line 110 without blending in air. It will be understood that the example of an inactive air intake line is provided for illustrative purposes and any other suitable mechanism may be used to reduce or prevent blending of nitrogen into the output gas.

In the high-oxygen supply mode 100b, the oxygen mass flow controller 114 is, as above, operated to provide a predetermined portion of oxygen for the mixed gas. To this end, the oxygen mass flow controller 114 may be fully open to practically operate as a mass flow meter, not restricting the flow of oxygen. The oxygen-air junction 118 is not supplied by air (and therefore not supplied with nitrogen) from the air intake line 110, and so merely provides a passage for the oxygen supply into the first gas output line 140. In addition, a portion of pure oxygen from the oxygen intake line 110 is allowed to flow, or diverted, via the first oxygen supply offtake 116, which is in an open condition 116a, into the second gas output line 150.

In the high-oxygen supply mode 100b, the first output mass flow controller 144 and the second output mass flow controller 152 both operate as mass flow controllers to control the flow of the supply gas, which in the high-oxygen supply mode may be pure or practically pure oxygen, as supply gas to two separate gas output lines. The oxygen mass flow controller 114 may also be used to modulate the oxygen supply entering the system. The applicant has appreciated that a sufficiently accurate modulation of the supply gas outputs may be achieved by the output mass flow controllers 144, 152 without relying on modulation by the oxygen mass flow controller 114.

It will be understood that the flow rate through the oxygen mass flow controller 114 is expected to correspond to the sum of the flow rates passing through the first output mass flow controller 144 and the second output mass flow controller 152. This provides an opportunity for the gas supply control system to incorporate a safety check in which control logic determines whether there is a deviation from the expected flow rates.

Both output mass flow controllers 144, 152 can be controlled independently. For instance, the second mass flow controller 152 may be closed such that oxygen is provided as output gas only through the first gas output line 140. In contrast to the mixed-gas supply mode, the second mass flow controller 152 is active to be able to modulate the flow of oxygen as output gas through the second gas output line 150 as soon as required.

The gas supply control system 100 may comprise a separate structure to shut off flow via the second gas output line 150 before it reaches the second output mass flow controller 152. In embodiments, the second output mass flow controller 152 may be positioned and controlled to allow it to fully close, to block gas supply through the second output mass flow controller 152, or to be modulatable to permit gas flow at a predetermined rate.

If carbon dioxide is required in the supply gas output, this can be introduced into the first gas output line 140 in the manner described in relation to FIG. 4 above. Initial calculations made by the Applicant indicate that the typical amounts of CO2 that may be required in a clinical scenario, e.g. for a pediatric patient, can be achieved by feeding carbon dioxide into only one of the gas output lines, e.g. into the first gas output line 140. Feeding carbon dioxide into only one of the gas output lines facilitates the sensor measurements and calculations for monitoring the gas composition(s) delivered to the oxygenator.

However, it will be understood that the gas supply control system could include a second feed of carbon dioxide (not illustrated in the Figures), to feed the second gas output line 150 in the manner described in relation to the first gas output line 140. By providing the carbon dioxide feed downstream of the first output mass flow controller 144, the sum of gas flowing through the first output mass flow controller 144 and the second output mass flow controller 152 can be expected to correspond to the flow passing the oxygen mass flow controller 114, whether or not carbon dioxide is subsequently blended into a gas line.

The above example discloses a gas supply control system that can be switched between two modes. In the first mode, a gas output is blended from a plurality (here: two or three) gas sources and provided via a single output line. In the second mode, a gas output is created using only oxygen, or mainly oxygen with optional components such as a carbon dioxide fraction, and distributed and provided via a plurality (here: two) output lines. However, it will be understood that the system may be operated in more than two modes, for instance to blend additional input gases into different compositions and supplying a different number of output lines. Likewise, while in the high-oxygen mode the system is described as supplying two output lines, it will be understood that any number of output lines may be provided, e.g. three, four or more output lines. The design of the gas supply control system may have to take into account the maximum flow rate and pressures of the gases supplied by the hospital environment.

The present gas supply control system is suitable for use with conventional single sweep supply (as illustrated in FIG. 1) and for multi-region sweep supply (such as the dual chamber supply illustrated in FIG. 2). For instance, in the mixed-gas supply mode 100*a*, the present gas supply control system 100 can be used with existing oxygenators, such as the exemplary oxygenator 1 of FIG. 1, by connecting the first gas output line 140 (FIG. 5) to modulate gas output to the sweep gas supply 4 (FIG. 1), and ensuring the second gas output line 150 is closed. The same system can be used, reconfigured in the high-oxygen mode 100*b*, by connecting e.g. the first gas output line 140 (FIG. 5) to modulate gas output to the first sweep gas supply 22 (FIG. 2) and the second gas output line 150 (FIG. 5) to modulate gas output to the second sweep gas supply 24 (FIG. 2).

The re-configuration from a single sweep supply capability to a multi-region sweep supply may be implemented by way of a simple switch, which may be carried out in software. This switch could open and close, respectively, the first oxygen supply offtake 116, the oxygen-air junction 118, and the operation of the oxygen mass flow controller 114, the first output mass flow controller and/or the second output mass flow controller 152.

This reduces the need to design two different systems for different supply gas control scenarios. At the same time, the design disclosed herein is relatively simple, requiring reconfiguration only of a few components and opening/closing a relatively small number of supply lines and offtakes. Thereby, the overall manufacturing and maintenance cost of the present gas supply control system may, despite its multi-functional aspects, not be much higher than the corresponding cost of conventional gas blenders.

The switch functionality (between the supply modes) could include a lock or manufacturer barrier to ensure the gas supply control system is not inadvertently switched to an inappropriate mode. As such, the gas supply control system could be locked in one of the supply modes (e.g. mixed-gas supply mode or high-oxygen supply mode), for instance in a manner allowing reconfiguration to another supply mode only during authorised maintenance.

The gas supply control system could comprise a sensor arrangement monitoring or activating an appropriate supply mode upon connection of a correspondingly configured oxygenator. For instance, the gas supply control system may detect whether or not a connection is made to the second gas output line 150. The detection may include checking if the connection is made with a permitted type of oxygenator. If an appropriate connection is made to the second gas output line 150, the gas supply control system may automatically switch to the high-oxygen supply mode, or it may present a message suggesting switching to the high-oxygen supply mode. If there is no appropriate connection detected to the second gas output line 150, the supply gas control system may block supply gas output via the second gas output line 150, e.g. by switching to the mixed-gas supply mode.

Figure 7:
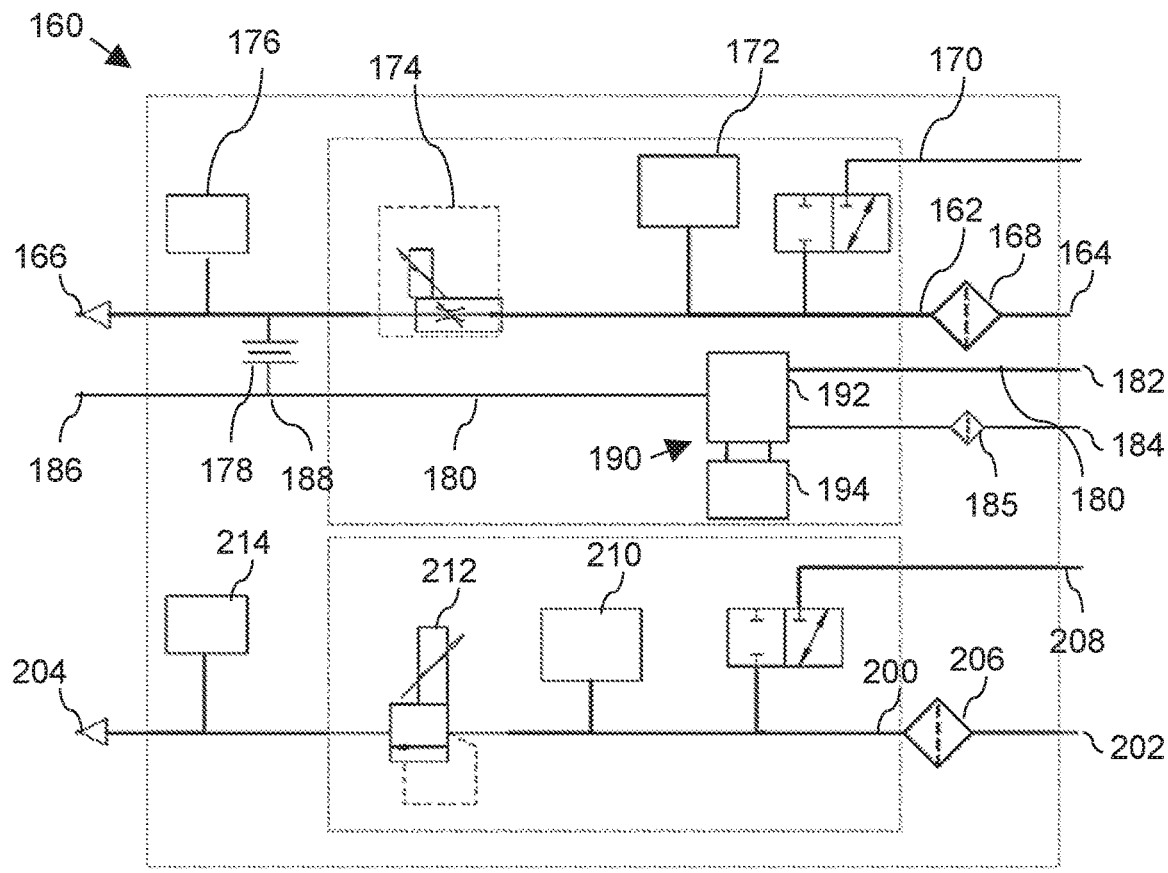
FIG. 7 shows a schematic diagram of a gas extraction system in accordance with the present disclosure.

FIG. 7 shows a gas extraction system 160. In FIG. 7 the general flow direction of exhaust gas is from the right to the left. The gas extraction system 160 comprises an exhaust gas removal line 162 whose upstream end 164 is to be connected to one or more exhaust ports of an oxygenator (not shown in FIG. 7) and whose downstream end 166 is connectable to an external exhaust suction port (not shown in FIG. 7). The external exhaust suction port may be referred to as "vacuum supply" to designate a source of flow-inducing low pressure. If the downstream end 166 is connected to an external exhaust suction port, it will be understood that this would apply a negative flow gradient encouraging flow of exhaust gas out of the oxygenator. Downstream of the upstream end 164 the line comprises a filter 168, an auxiliary vent 170, an exhaust line pressure sensor 172, and exhaust line mass flow controller 174 and a suction pressure sensor 176. The sensors and flow controllers allow the exhaust gas flow rate to be controlled and modulated.

The gas extraction system 160 comprises a sampling line 180 separately to the exhaust gas removal line 162 in which a sensor array 190 is provided to allow the condition of the exhaust gas to be monitored. The sampling line 180 comprises an upstream end 182 connectable to the exhaust end of an oxygenator, either directly to an oxygenator or to an offtake of the exhaust port, to allow exhaust gas to be collected and/or diverted into the sampling line 180 and to the sensor array 190. The sampling line 180 may further comprise a reference line 184, with a filter 185, upstream of the sensor array 190 to provide a reference supply to the sensor array 190.

The sensor array 190 comprises several sensors, as may be required in a clinical case, such as a carbon dioxide sensor, an anaesthetic agent sensor, or an oxygen sensor. The sensors may be grouped as a sensor arrangement 192. Some or all of the sensors may be placed separately from the sensor arrangement 192, indicated in FIG. 7 by a sensor location 194. For instance, certain sensor types may require regular maintenance, such as replenishment with a consumable component. Such sensor types may be located in a manner facilitating regular maintenance in the sensor location 194, for instance they may be located close to an access port in a device housing (e.g. housing 20 depicted in FIG. 3).

The downstream end 186 of the sampling line may vent into the atmosphere and as such may be a simple opening or port permitting gas that passed through the sampling line 180 to exit the gas extraction system. Upstream of the downstream end 186 and downstream of the sensor array 190, a diversion 188 links the sampling line 180 into the exhaust gas removal line 162, allowing the same exhaust gas suction port, or "vacuum source", to be used for the creation of a negative flow gradient in both the exhaust gas removal line 162 and the sampling line 180.

Between the sensor array 190 and the downstream end 166 of the exhaust gas removal line 162 (here indicated in the diversion 188), a flow restrictor 178 is provided. The flow restrictor 178 may be provided as a pressure drop plate and allows the flow and/or pressure conditions at the sensor array 190 to be isolated, to a certain degree, at least in a portion of the sampling line 180 from the exhaust gas removal line 162.

The provision of a flow restrictor 178 avoids that the gas flow conditions across the sensor array 190 are adversely, or uncontrollably, influenced by the exhaust gas suction source, e.g. by the strength and/or fluctuations in strength of the exhaust gas suction source. This is believed to be helpful for sensors relying on predefined gas conditions such as on a pre-defined gas flow rate. The flow restrictor may also facilitate, and practically ensure, atmospheric pressure conditions in the sampling line 180, particularly in the portion of the sampling line 168 in which the sensor array 190 is located, while suction is applied at the downstream end 166. However, the flow restrictor 178 still allows a certain limited amount of suction for gas passing the sampling line 180 to be diverted by way of the hospital exhaust suction source so that it may be collected together with the main exhaust gas, if this is required to collect anaesthetic gas. Thereby, the entire exhaust gas can be directed via the downstream end 166 if this is required for compliance with anaesthesia treatment protocols.

The gas extraction system 160 further comprises a vacuum-assisted venous drainage line 200 whose upstream end 202 is to be connected to a venous drainage system (not shown in FIG. 7) and whose downstream end 204 is connectable to an external drainage suction port (not shown in FIG. 7). The vacuum-assisted venous drainage line 200 comprises a filter 206, an auxiliary vent 208, a pressure sensor 210, a proportional vacuum regulator 212 and a suction pressure sensor 214. The sensors and flow controllers allow the pressure level for venous drainage to be controlled and modulated.

The downstream end 204 of the vacuum-assisted venous drainage line is connectable to a drainage suction port independently of the downstream end 166 of the exhaust gas removal line 162. As such, the pressure and flow conditions in the exhaust gas removal line 162 and in the vacuum-assisted venous drainage line 200 can be modulated independently of each other.

The present disclosure includes, therefore, a gas extraction system for an extracorporeal ventilation system capable of providing assisted venous drainage, wherein the gas extraction system comprises a drainage-assisting line for connection to a first external hospital suction supply, and further comprises a waste gas removal line for connection to a second external hospital suction supply, and wherein the gas extraction system further comprises a control system allowing the waste gas removal line to be operated at a higher flow rate than the drainage assisting line and/or allowing the drainage assisting line to be operated at a lower pressure, causing stronger suction, than the waste gas removal line. Optionally, the gas supply control system comprises a configuration allowing it to operate the assisted venous drainage independently of the connection of the waste gas removal line to the second hospital suction supply.

An external exhaust suction port, connected to the downstream end 166 of the exhaust gas removal line 162, may be used to direct a flow of exhaust gas, e.g. towards a waste anaesthetic gas collection, to avoid that waste anaesthetic gas enters the operating theatre via an oxygenator exhaust port. In scenarios in which a patient is sedated without anaesthesia gas, it may not be necessary to apply exhaust gas suction for the purpose of anaesthesia treatment. Indeed the clinical infrastructure may not provide a suitable exhaust gas suction if local clinical practice does not rely on the oxygenation gas for anaesthesia. The gas extraction system 160 permits the exhaust gas removal line 162 to be connected to an external exhaust gas suction port if waste anaesthesia gas collection is required, but likewise is able to allow exhaust gas to vent or to be collected at normal flow rates if waste anaesthesia gas collection is not required. The operation and control of the vacuum-assisted venous drainage line 200 is unaffected by the presence and type of exhaust gas suction, which simplifies the management of venous drainage.

With regard to the location of the sensor array 190, certain sensor types require that the oxygen content is measured at specific parameters, such as gas flow rate and flow conditions (e.g., laminar rather than turbulent), temperature, water content or pressure. If the exhaust gas contains waste anaesthesia gas, then the exhaust gas is collected using a negative pressure gradient, which may pose a challenge to providing an exact measurement in a waste anaesthetic gas collection line. The present Applicant has developed the present arrangement to allow a full array of sensors to be used, including sensors that require or are calibrated for use at atmospheric pressure and/or low flow rates, whether or not the exhaust gas removal line is connected to a negative pressure exhaust gas suction source that may provide pressure and flow conditions that are outside the sensor specifications. Isolating the sampling line to some extent from direct exposure to the exhaust line flow conditions allows a wider selection of sensors to be used in the system. Furthermore, the present gas extraction system can be used in settings with and without anaesthetic gas collection, because the sampling line 180 can be operated in isolation of the pressure and/or flow conditions created by a hospital exhaust section port. This allows the same design of a gas extraction system to be used for many hospital designs.

It will be understood that any suitable flow control mechanism may be used instead of the exemplary mass flow controllers described herein. The flow controllers may be set to operate at a pre-defined setpoint, and the flow rate and or setpoint for each flow controller may be modulatable to maintain the flow rate through a sensor at a desired level.

The filters, such as filters 111, 121, 131, 168 and 206 are described herein to illustrate their likely relative position within the control systems. However, it will be understood that the filters are not necessarily essential to the operation of the principles described herein.

The oxygenation system may comprise and/or be connected to a controller and software instructions implemented by the processor. Any one or more of the method steps may be carried out by a controller.

Also described herein is a method of controlling the gas supply to an oxygenator of an extracorporeal ventilation system. The method comprises providing a connection to external gas supply ports to receive supplied oxygen and supplied nitrogen, providing two or more gas output lines, creating a supply gas output from a predetermined portion of supplied oxygen and from a predetermined portion of supplied nitrogen, and a supply of oxygen gas, and supplying one or more of the gas output lines with the supply gas output.

In some embodiments, the method comprises supplying two or more of the gas output lines with the supply gas output.

The supplied nitrogen may be supplied in the form of supplied air. The predetermined portion of supplied nitrogen may be no nitrogen.

In some embodiments, the method comprises modulating the flow rates through at least two of the gas output lines differently.

In some embodiments, the method comprises blocking supply gas output through one or more gas output lines while maintaining supply gas output through at least one of the gas output lines.

In some embodiments, the method comprises supplying only one of the gas output lines with the supply gas output.

In some embodiments, the method comprises providing a connection to external gas supply ports to receive supplied carbon dioxide and creating a supply gas output from a predetermined portion of supplied carbon dioxide.

In some embodiments, the method comprises blending supply gas with a predetermined portion of supplied carbon dioxide after blending supplied nitrogen and supplied oxygen.

In some embodiments, the method comprises creating the supply gas output using only, or practically only, supplied oxygen. The supply gas may be blended with a predetermined portion of supplied carbon dioxide. In that case, the supply gas output is blended from a predetermined portion of supplied oxygen and a predetermined portion of supplied carbon dioxide.

In some embodiments, the method comprises measuring the flow rate of the predetermined portion of oxygen, of the predetermined portion of nitrogen, and of the supply gas output, and determining whether or not the flow rate of the supply gas output corresponds to a sum of the flow rate of the predetermined portion of supplied oxygen and of the flow rate of the predetermined portion of supplied nitrogen.

In some embodiments, the method comprises measuring the flow rate of the supply gas output before blending a predetermined portion of carbon dioxide into the supply gas output.

In some embodiments, the method comprises measuring the flow rate of the predetermined portion of supplied oxygen and of the supply gas output through each gas output line, and determining whether or not the flow rate of the predetermined portion of the supplied oxygen corresponds to a sum of the flow rates through each gas output line.

In some embodiments, the method comprises operating the gas supply in a mixed-gas supply mode or in a high-oxygen supply mode, wherein in the mixed-gas supply mode the gas output is created from supplied oxygen mixed with supplied nitrogen and wherein in the high-oxygen supply mode the gas output is created from supplied oxygen.

It will be understood that the gas output in the high-oxygen supply mode comprises less nitrogen than in the mixed-gas supply mode, and may comprise no or practically no nitrogen.

The method may comprise switching to the mixed-gas supply mode when supplying an oxygenator with a single gas-blood interface region. The method may comprise switching to the high-oxygen supply mode when supplying an oxygenator with a multi-region gas-blood interface.

In some embodiments, the method comprises supplying a first number of gas output lines in the mixed-gas supply mode and supplying a second number of gas output lines that differs from the first number of gas output lines in the high-oxygen supply mode.

In some embodiments, the method comprises supplying one gas output line in the mixed-gas supply mode. In some embodiments, the method comprises supplying each gas output line in the high-oxygen supply mode.

Further described herein is a method of extracting gas from an extracorporeal ventilation system comprising an exhaust gas removal line, wherein the method comprises providing a connection for the exhaust gas removal line to an external exhaust suction port, diverting a portion of the exhaust gas via a sampling line, and providing a passage allowing the portion of exhaust gas diverted via the sampling line to flow to the exhaust gas removal line. The method also comprises providing the sampling line with an outlet port for passively venting the portion of exhaust gas not flowing to the exhaust gas removal line.

The method may comprise connecting the exhaust gas removal line to the external exhaust suction port and thereby causing exhaust gas to flow via the exhaust gas removal line towards the exhaust suction port and causing a the portion of exhaust gas to flow via the sampling line towards the exhaust suction port.

If the exhaust gas removal line is not connected to an external exhaust suction port, the method may comprise letting the portion of exhaust gas diverted via the sampling line vent via the outlet port.

In some embodiments, the method comprises providing a flow restrictor to reduce the flow rate in at least a portion of the sampling line when suction from the exhaust suction port is applied to it.

In some embodiments, the method comprises measuring gas parameters in the portion of the sampling line with reduced flow.

In some embodiments, the method comprises providing an assisted venous drainage line for connection to the drainage suction port. In some embodiments, the method comprises maintaining the connection of the drainage suction port to the assisted venous drainage line isolated from the exhaust gas removal line.

In some embodiments, the method comprises modulating the flow rate of the drainage line differently from the flow rate of the exhaust gas removal line.

In some embodiments, the method comprises modulating the suction pressure of the drainage line differently from the suction pressure of the exhaust gas removal line.

The methods described herein may comprise providing and/or operating any one of the components of the gas supply control system and of the gas extraction system.

Some of the method steps described herein may be carried out in software.

The invention claimed is:

1. A gas supply control system for an oxygenator of an extracorporeal ventilation system, the gas supply control system comprising:
   a plurality of inlets for connection to external gas supply ports to receive supplied oxygen and supplied nitrogen;
   a gas supply device, in fluid communication with the plurality of inlets, having a configuration allowing it to create a supply gas output from a predetermined portion of supplied oxygen and from a predetermined portion of supplied nitrogen;
   two or more gas outlets from the gas supply device; and
   wherein the gas supply device further includes a configuration allowing it to switch between a mixed-gas supply mode and a high-oxygen supply mode, wherein in the mixed-gas supply mode the supply gas output is provided through one of the gas outlets and is created from supplied oxygen mixed with supplied nitrogen, and in the high-oxygen supply mode the supply gas output is provided through a plurality of the gas outlets and is created from supplied oxygen, wherein the supply gas output in the high-oxygen supply mode contains less nitrogen than in the mixed-gas supply mode.

2. The gas supply control system according to claim 1, wherein the gas supply device further includes a configuration allowing it to modulate flow rates through the gas outlets differently.

3. The gas supply control system according to claim 1, operable in a configuration blocking supply gas output through one or more of the gas outlets and maintaining supply gas output through at least one of the gas outlets.

4. The gas supply control system according to claim 1, further configured for connection to an external gas supply port to receive supplied carbon dioxide, wherein the gas supply control system is operable in a configuration allowing it to create the supply gas output comprising a predetermined portion of supplied carbon dioxide.

5. The gas supply control system according to claim 4, configured to blend supply gas with a predetermined portion of supplied carbon dioxide after blending supplied nitrogen and supplied oxygen.

6. The gas supply control system according to claim 1, operable in a configuration allowing it to create the supply gas output using only supplied oxygen.

7. The gas supply control system according to claim 1, further comprising a sensor arrangement allowing it to determine flow rates of the predetermined portion of supplied oxygen, the predetermined portion of supplied nitrogen, and of the supply gas output, wherein the gas supply control system further comprises control logic allowing it to determine whether or not the flow rate of the supply gas output corresponds to a sum of the flow rate of the predetermined portion of supplied oxygen and of the flow rate of the predetermined portion of supplied nitrogen.

8. The gas supply control system according to claim 7, configured to blend supply gas with a predetermined portion of supplied carbon dioxide after blending supplied nitrogen and supplied oxygen, and wherein the sensor arrangement comprises a sensor to determine the flow rate of the supply gas output, the sensor being positioned upstream of the feed for blending a predetermined portion of carbon dioxide into the supply gas output.

9. The gas supply control system according to claim 1, further comprising a sensor arrangement allowing it to determine flow rates of the predetermined portion of supplied oxygen, and of the supply gas output through each gas outlet, wherein the gas supply control system further comprises control logic allowing it to determine whether or not the flow rate of the predetermined portion of the supplied oxygen corresponds to a sum of the flow rates through each gas outlet.

10. The gas supply control system according to claim 1, comprising a gas pressure sensor arrangement, wherein each of the gas outlets is connected to a gas output line that comprises an individual output pressure sensor and a vent individually actuatable in the event of an adverse pressure measurement in the respective gas output line.

11. An extracorporeal oxygenation system comprising:
    an oxygenator; and
    a gas supply control system, the gas supply control system including:
       a plurality of inlets for connection to external gas supply ports to receive supplied oxygen and supplied nitrogen,
       a gas supply device, in fluid communication with the plurality of inlets, having a configuration allowing it to create a supply gas output from a predetermined portion of supplied oxygen and from a predetermined portion of supplied nitrogen,
    two or more gas outlets from the gas supply device; and
    wherein the gas supply device further includes a configuration allowing it to switch between a mixed-gas supply mode and a high-oxygen supply mode, wherein in the mixed-gas supply mode the supply gas output is provided through one of the gas outlets and is created from supplied oxygen mixed with supplied nitrogen, and in the high-oxygen supply mode the supply gas output is provided through a plurality of the gas outlets and is created from supplied oxygen, wherein the supply gas output in the high-oxygen supply mode contains less nitrogen than in the mixed-gas supply mode.

12. The extracorporeal oxygenation system according to claim 11 wherein the oxygenator comprises a single sweep gas inlet, and wherein one of the gas outlets is connected to the sweep gas inlet and the gas supply control system is configured to supply the one gas outlet with a supply gas output.

13. The extracorporeal oxygenation system according to claim 11, wherein the oxygenator comprises a plurality of sweep gas inlets, and wherein each of the sweep gas inlets is connected to a gas outlet of the gas supply control system.

14. The extracorporeal oxygenation system according to claim 11, further comprising a gas extraction system, the gas extraction system comprising an exhaust gas removal line for connection to an external exhaust suction port, wherein the gas extraction system further comprises a sampling line and a connection merging the sampling line and the exhaust gas removal line to allow suction from the exhaust suction port to be applied to the sampling line, and wherein the sampling line comprises an outlet port for passively venting when not connected to the exhaust suction port.

15. The gas supply control system according to claim 1, wherein in the high-oxygen supply mode the supply gas output is provided through each of the two or more gas outlets.

16. The gas supply control system according to claim 1, wherein the supply gas output in the high-oxygen supply mode contains negligible nitrogen.

17. The gas supply control system according to claim 1, wherein the supply gas output in the high-oxygen supply mode is pure oxygen.

18. The gas supply control system according to claim 1, wherein the supply gas output in the high-oxygen supply mode is pure oxygen blended with carbon dioxide.

19. The extracorporeal oxygenation system according to claim 17, wherein the supply gas output in the high-oxygen supply mode contains negligible nitrogen.

20. The extracorporeal oxygenation system according to claim 17, wherein the oxygenator comprises a plurality of separately supplyable interface regions, and wherein in the high-oxygen supply mode each interface region is supplied with supply gas by a respective one of the plurality of gas outlets.

* * * * *